US011266397B2

(12) United States Patent
Balboa et al.

(10) Patent No.: US 11,266,397 B2
(45) Date of Patent: Mar. 8, 2022

(54) SUTURE ANCHOR ASSEMBLIES AND METHODS OF USE THEREOF

(71) Applicants:Smith & Nephew, Inc., Memphis, TN (US); Smith & Nephew Orthopaedics AG, Zug (CH); Smith & Nephew Asia Pacific Pte. Limited, Singapore (SG)

(72) Inventors: Marc Joseph Balboa, Hopkinton, MA (US); Mark Edwin Housman, North Attleboro, MA (US); Jon-Paul Rogers, North Smithfield, RI (US); Jason Hamilton, Dartmouth, MA (US); Kyle Turner, Mansfield, MA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 302 days.

(21) Appl. No.: 16/776,634

(22) Filed: Jan. 30, 2020

(65) Prior Publication Data
US 2020/0245997 A1 Aug. 6, 2020

Related U.S. Application Data

(60) Provisional application No. 62/800,797, filed on Feb. 4, 2019.

(51) Int. Cl.
*A61B 17/04* (2006.01)

(52) U.S. Cl.
CPC .... *A61B 17/0401* (2013.01); *A61B 2017/044* (2013.01); *A61B 2017/0409* (2013.01);
(Continued)

(58) Field of Classification Search
CPC ........ A61B 17/0401; A61B 2017/0496; A61B 2017/0412; A61B 2017/0445; A61B 2017/0453; A61B 2017/0414; A61B 2017/0464; A61B 2017/0409; A61B 2017/044
See application file for complete search history.

(56) References Cited

U.S. PATENT DOCUMENTS 7,828,820 B2 * 11/2010 Stone ................. A61B 17/0401
606/232
9,314,240 B2 * 4/2016 Paulk ................. A61B 17/0401
(Continued)

FOREIGN PATENT DOCUMENTS

| CN | 207886227 U | 9/2018 |
|----|----|----|
| EP | 2498687 B1 | 6/2020 |
| WO | 2011060022 | 5/2011 |

OTHER PUBLICATIONS

Search report for corresponding EP application No. 20152843.7 dated Jun. 30, 2020.

*Primary Examiner* — Phong Son H Dang
(74) *Attorney, Agent, or Firm* — Burns & Levinson, LLP; Joseph M. Maraia; Marlo Schepper Grolnic (57) ABSTRACT

A suture anchor assembly includes an eyelet of a pound-in tip formed through both of a distal portion and a proximal portion of the tip. An anchor body of the assembly is configured to be inserted over the proximal portion of the tip such that it partially occludes the tip eyelet, allowing for a shorter overall total length of the anchor assembly.

10 Claims, 6 Drawing Sheets

(52) U.S. Cl.
CPC ............ *A61B 2017/0445* (2013.01); *A61B 2017/0464* (2013.01); *A61B 2017/0496* (2013.01)

(56) References Cited

U.S. PATENT DOCUMENTS

| | | | |
|---|---|---|---|
| 9,936,939 B2 * | 4/2018 | Nguyen | A61B 17/0401 |
| 9,980,718 B2 * | 5/2018 | Housman | A61B 17/8645 |
| 10,111,652 B2 * | 10/2018 | Patel | A61B 17/0401 |
| 2004/0138706 A1 * | 7/2004 | Abrams | A61B 17/0401 606/232 |
| 2006/0276841 A1 * | 12/2006 | Barbieri | A61B 17/0401 606/232 |
| 2008/0009904 A1 * | 1/2008 | Bourque | A61B 17/0401 606/232 |
| 2009/0112270 A1 * | 4/2009 | Lunn | A61F 2/0811 606/301 |
| 2009/0157124 A1 * | 6/2009 | Ferragamo | A61B 17/0643 606/301 |
| 2010/0016902 A1 * | 1/2010 | Paulk | A61B 17/0401 606/300 |
| 2013/0006302 A1 * | 1/2013 | Paulk | A61B 17/0401 606/232 |
| 2014/0364905 A1 | 12/2014 | Lunn et al. | |

\* cited by examiner

SUTURE ANCHOR ASSEMBLIES AND METHODS OF USE THEREOF

CROSS-REFERENCE TO RELATED APPLICATIONS

This application claims priority to and benefit of U.S. Provisional Application No. 62/800,797, filed Feb. 4, 2019, entitled SUTURE ANCHOR ASSEMBLIES AND METHODS OF USE THEREOF, the contents of which in are incorporated herein by reference in their entirety for all purposes.

FIELD

The present disclosure relates to tissue repair, and more specifically, to an anchor assembly for securing tissue to bone.

BACKGROUND

Arthroscopic procedures often require soft tissue to be reattached to bone. To achieve this, anchors are placed in the bone and sutures attached to the anchor are passed through the tissue to securely retain the tissue in place. Typical anchors may be pound-in or screw-in type anchors, or combinations of both.

Some examples of combination-type anchors consist of a distal anchor tip, which is pounded into the bone, and a proximal anchor body, which is screwed into the bone. A distal portion of the tip may have an eyelet which receives suture before the tip and the suture are inserted into a bone hole. The anchor body may then be delivered into the bone hole up to, but not covering, the eyelet.

When inserted into the bone hole, the combined lengths of the tip and the anchor body amount to a given total length. It is therefore advantageous to have this total length be as small as possible to allow for a shallower hole preparation. A shallower hole preparation removes less bone and is therefore less traumatic to the patient. It is also less likely that a surgeon will mistakenly contact other anatomy while preparing a shallower bone hole.

SUMMARY

Described herein is a combination-type anchor assembly in which an eyelet of the pound-in tip is formed through both of a distal portion and a proximal portion of the tip. The anchor body of the assembly is configured to be inserted over the proximal portion of the tip such that it partially occludes the tip eyelet. This allows for a larger eyelet to be defined through the tip, which advantageously allows a greater amount of suture be passed through the eyelet for securing tissue. Furthermore, it allows for a shorter length of the tip, which reduces the overall total length of the anchor assembly. This in turn beneficially allows for a shallower hole preparation.

Further examples of the anchor assembly of this disclosure may include one or more of the following, in any suitable combination.

In examples, an anchor assembly of this disclosure includes a tip having a distal portion and a proximal portion. A cavity is defined within the tip, with a wall of the cavity having threads. An opening of the cavity is located in the proximal portion of the tip. A through hole extends through the tip with a first region defined in the distal portion a the tip and a second region defined in the proximal portion of the tip. A plug having outer threads is disposed within the cavity of the tip such that the threads of a distal region of the plug are engaged with the threads of the cavity and a proximal region of the plug extends from the opening of the cavity. An anchor body is disposed about the proximal portion of the tip and encloses the proximal region of the plug. The second region of the through hole is covered by the anchor body and the first region of the through hole is not covered by the anchor body.

In further examples, the through hole extends through the tip transverse to a longitudinal axis of the cavity. In examples, the plug includes a cannulation. In examples, the anchor body includes a threaded proximal outer portion and a non-threaded distal outer portion. In examples, the non-threaded distal outer portion of the anchor body is coupled to the proximal portion of the tip. In examples, the tip includes a protrusion disposed about an annular surface between the distal portion and a proximal portion of the tip. In examples, an outer diameter of the protrusion is selected to be larger than an outer diameter of the non-threaded distal outer portion of the anchor body. In examples, the through hole is in communication with the cavity defined within the tip. In examples, a distal end of the plug is unthreaded.

In yet further examples, the anchor assembly includes an anchor delivery device having a handle with a proximal end and a distal end. A first knob is coupled to the distal end of the handle and a second knob is coupled to the proximal end of the handle. A shaft is also coupled to the handle. The shaft includes an outer member, an inner member disposed within the outer member, and a driver disposed within the inner member. A proximal portion of the driver is coupled to the first knob and a proximal portion of the outer member is coupled to the second knob. The anchor body is coupled to a distal portion of the outer member, the tip is coupled to a distal portion of the inner member, and the plug is coupled to a distal portion of the driver.

In examples, a method of tissue repair of this disclosure includes creating a bone hole in bone. A suture is passed through a through hole of a tip of an anchor assembly. The through hole has a first region defined in a distal portion of the tip and a second region defined in a proximal portion of the tip. The anchor assembly further includes a cavity defined within the tip, with a wall of the cavity having threads. An opening of the cavity is located in the proximal portion of the tip. A plug having outer threads is at least partially located within the cavity of the tip. An anchor body includes a cavity for receiving the proximal portion of the tip. The tip of the anchor assembly is inserted into the bone hole and the plug is axially advanced to engage the suture within the through hole of the tip. The anchor body is advanced within the bone hole such that a distal end of the anchor body covers the proximal end of the tip and occludes the proximal region of the through hole.

In examples, the method further includes tensioning the suture prior to advancing the plug to engage the suture. In examples, the method further includes attaching the suture to soft tissue. In examples, the through hole extends through the tip transverse to a longitudinal axis of the cavity. In examples, the plug includes a cannulation. In examples, the anchor body includes a threaded proximal outer portion and a non-threaded distal outer portion. In examples, the tip includes a protrusion disposed about an annular surface between the distal portion and a proximal portion of the tip. In examples, an outer diameter of the protrusion is selected to be larger than an outer diameter of the non-threaded distal outer portion a the anchor body. In examples, the through hole is in communication with the cavity defined within the tip. In examples, a distal end of the plug is unthreaded.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Figure 1:
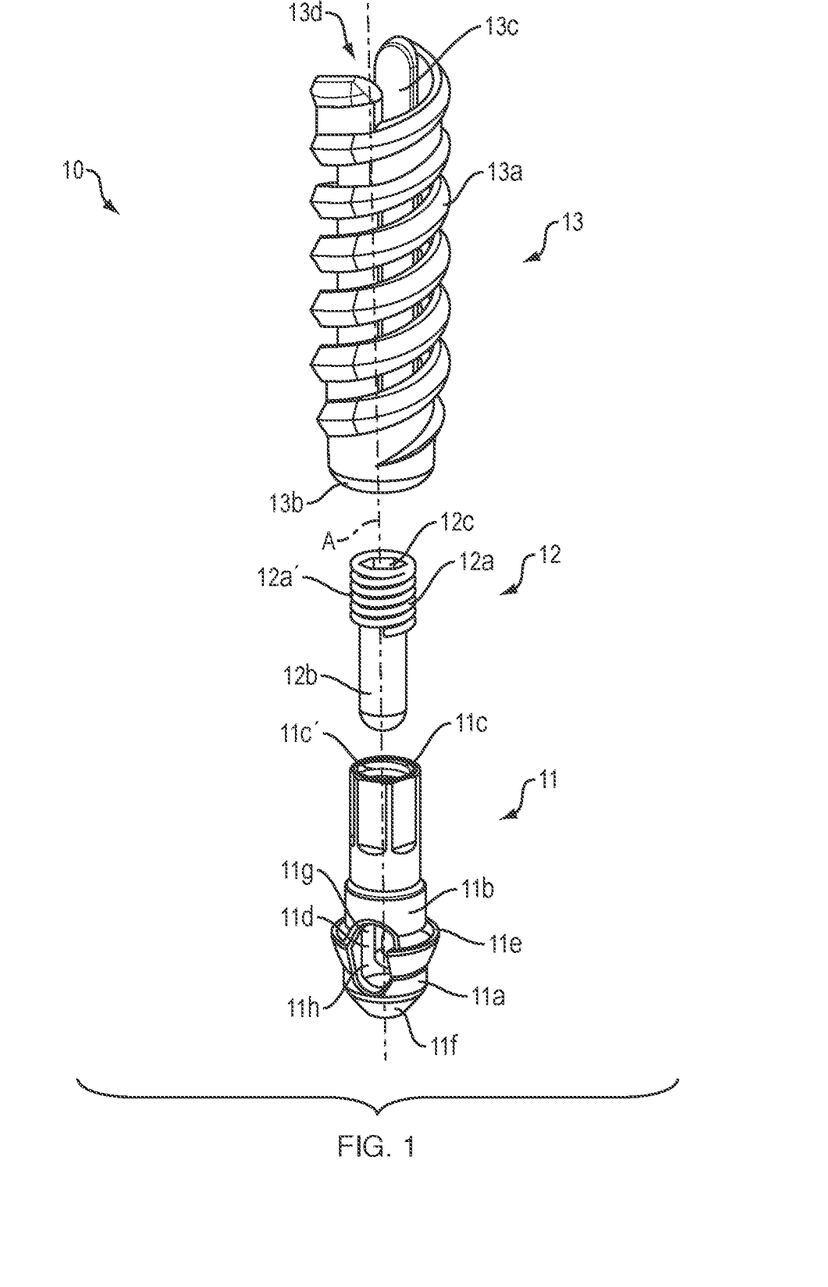
FIG. 1 is an exploded view of the anchor assembly of the present disclosure.

Turning now to FIG. 1, the components of the anchor assembly 10 of the present disclosure are illustrated in an exploded view. As shown in FIG. 1, the anchor assembly 10 generally includes an anchor tip 11, a plug 12, and an anchor body 13. The tip 11 may be configured for pounding into bone, while the anchor body 13 may be configured for screwing into the bone. However, it is also contemplated that the anchor body 13 could be configured for pounding into bone. The plug 12 is configured for locking a suture within the tip 11, as further described below. The anchor assembly 10 may be used in a tissue repair, such as the tissue repairs described in U.S. Publication No. 2009/0112270 to Lunn et al., U.S. Publication No. 2010/0016869 to Paulk et al., and U.S. Publication No. 2010/0016902 to Paulk et al., the disclosures of which are incorporated herein by reference in their entireties.

As shown in FIG. 1, the tip 11 includes a distal portion 11a and a proximal portion 11b. A tip cavity 11c is defined within the tip 11 extending along a longitudinal axis A. The tip cavity 11c includes an opening 11c' at the proximal end of the tip 11 for receiving the plug 12 within the tip cavity 11c. A through hole 11d extends through the tip 11 transverse to the longitudinal axis A of the tip cavity 11c and is in communication with the tip cavity 11c. The through hole includes a first region 11g defined through the proximal portion 11b of the tip 11 and a second region 11h defined through the distal portion 11a of the tip 11. A protrusion 11e extends from the outer surface of the tip 11 between the distal portion 11a and the proximal portion 11b of the tip 11. In examples, the protrusion 11e is a semi-annular protrusion extending around the circumference of the tip 11 between openings of the through hole 11d. Examples of the tip 11 may also include barbs (not shown) located on the outer surface of the distal portion 11a of the tip 11 for reducing pull-out forces once the tip 11 has been inserted into bone. A distal end 11f of the tip 11 may be pointed, for creation of a bone hole, or may be blunt as shown, for cases where a bone hole is created prior to insertion of the tip 11.

In examples, a proximal portion 12a of the plug 12 includes threads 12a', and a distal portion 12b of the plug is non-threaded. However, it is contemplated that the distal portion 12b of the plug 12 may also include threads. The plug 12 also includes an internal cannulation 12c extending through the plug 12 along the longitudinal axis A. The tip cavity 11c includes threads that engage a distal portion of the threads 12a' of the plug 12 upon insertion of the plug 12 into the tip cavity 11c, while the remainder of the plug 12 extends outside of the tip cavity 11c.

Still referring to FIG. 1, examples of the anchor body 13 include a threaded proximal portion 13a configured for screwing the anchor body 13 into bone, and a non-threaded distal portion 13b. An anchor body cavity 13c is defined within the anchor body 13 extending along the longitudinal axis A. The anchor body cavity 13c includes an opening 13d at the proximal end of the anchor body 13 for receiving a portion of a delivery device, as further described below. A diameter of the anchor body cavity 13c at the distal portion 13b of the anchor body 13 is selected such that the anchor body 13 may be advanced over the proximal portion 11b of the tip 11 up to the protrusion 11e, thus covering the proximal region 11g of the through hole 11d. In examples, an outer diameter of the protrusion 11e is selected to be larger than an outer diameter of the non-threaded distal portion 13b of the anchor body 13. Thus, the protrusion 11e prevents further axial advancement of the anchor body 13 over the tip 11.

Figure 2:
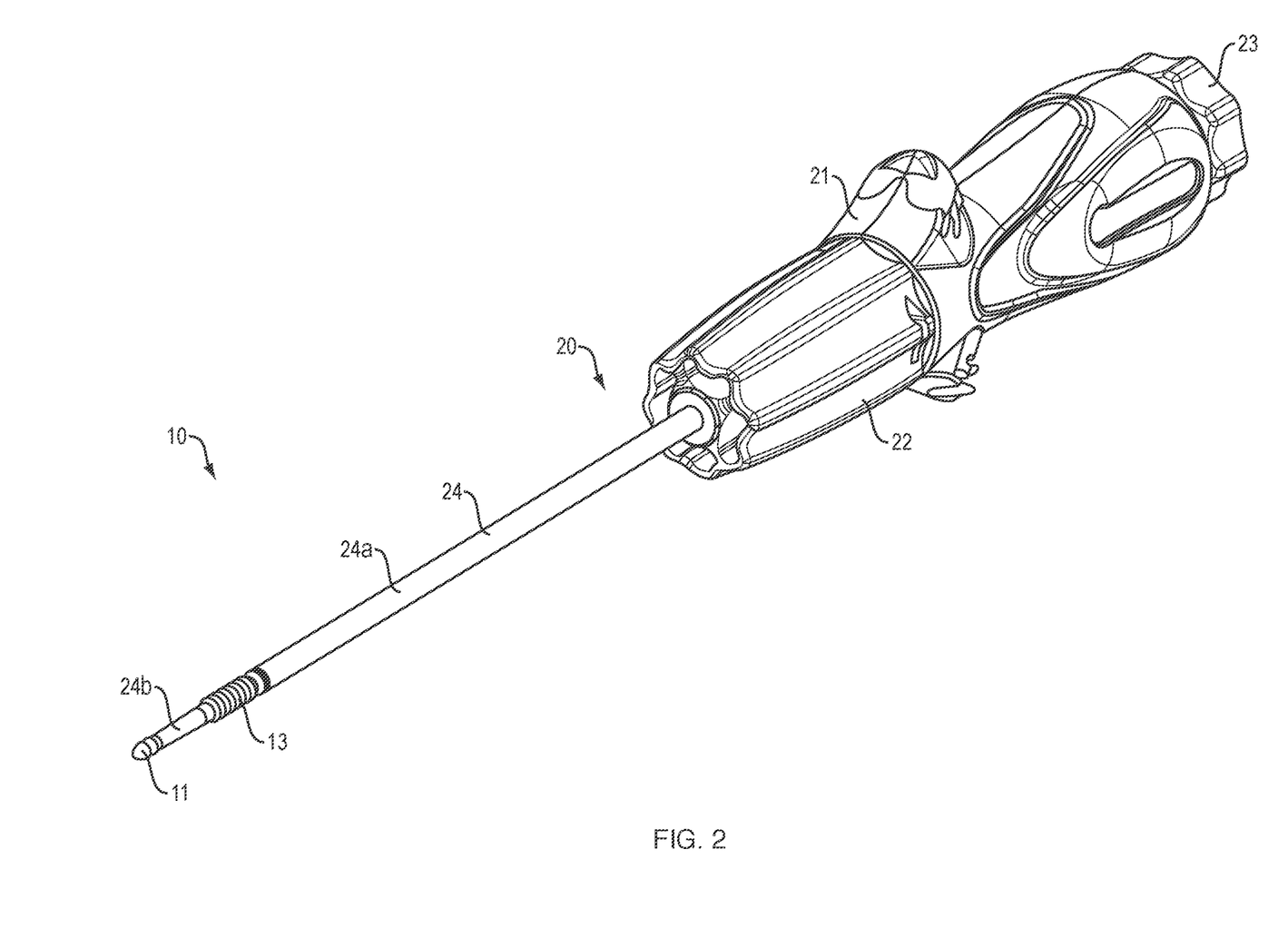
FIG. 2 is an isometric view of the anchor delivery device and the anchor assembly of the present disclosure.

Turning now to FIG. 2, a delivery device 20 for inserting the anchor assembly 10 of FIG. 1 into bone is shown in an isometric view. The delivery device 20 includes a handle 21, a first first knob 22 coupled to the distal end of the handle 21 and a second knob 23 coupled to the proximal end of the handle 21. A shaft 24 including an outer member 24a and an inner member 24b disposed within the outer member 24a are also coupled to the handle 21. When engaged with the delivery device 20, the anchor body 13 of the anchor assembly 10 is coupled to the outer member 24a and the tip is coupled to the inner member 24b. A driver 25 (FIG. 3) is furthermore disposed within the inner member 24*b* for engagement with the plug 12, as further described below.

Figure 3:
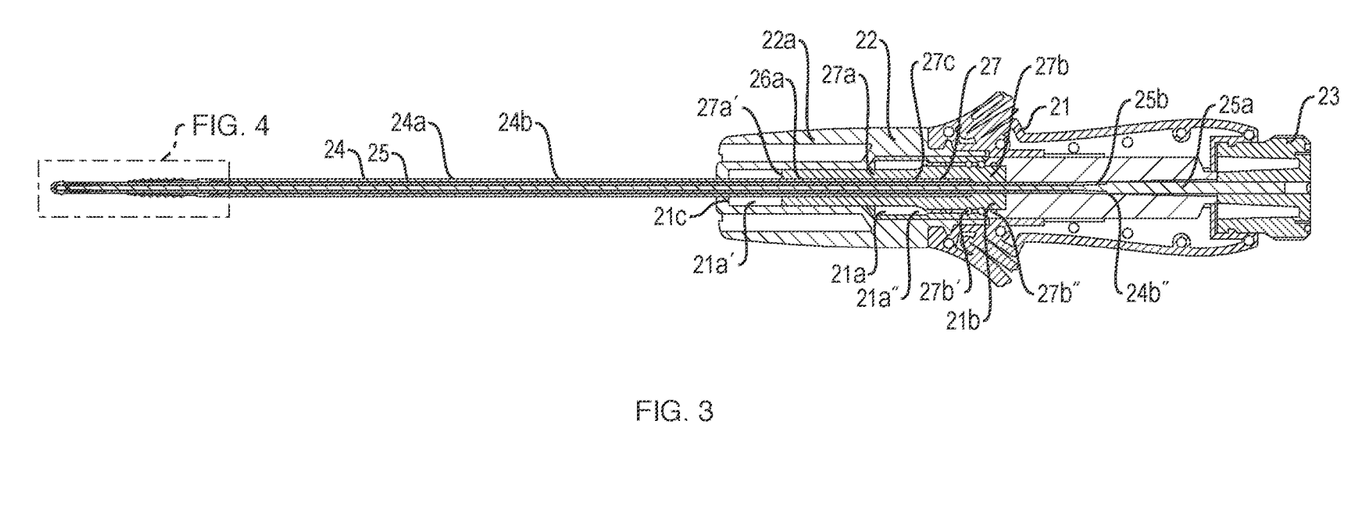
FIG. 3 is a cross-sectional view of the anchor delivery device of FIG. 2 prior to insertion of the anchor assembly into bone.
Figure 4:
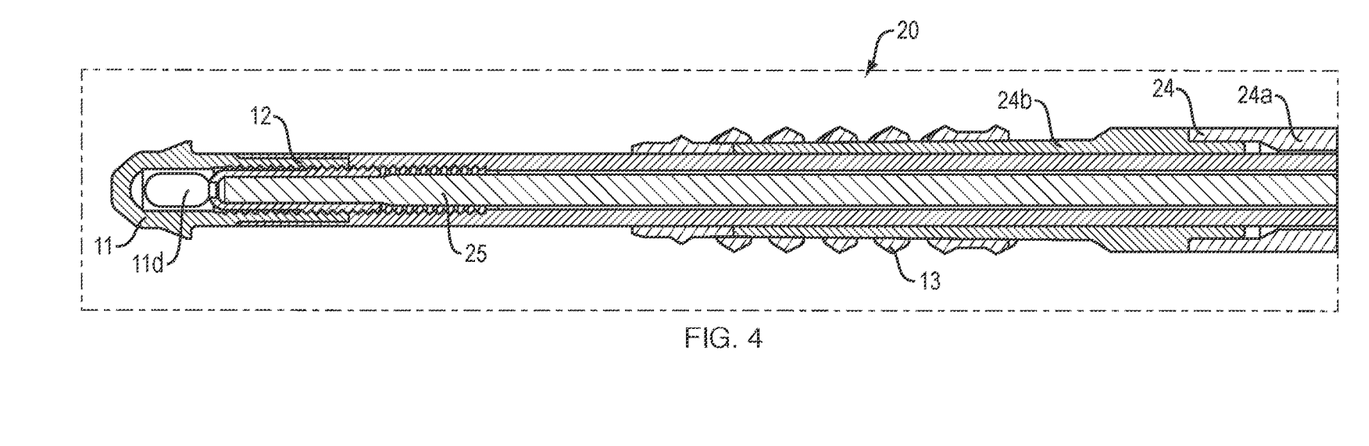
FIG. 4 is an expanded view of the distal end of the shaft of the anchor delivery device of FIG. 3.

Turning now to FIGS. 3 and 4, cross-sections of the delivery device 20 before insertion of the anchor 10 into bone are shown. The proximal portion 25*a* of the driver 25 is coupled to the second knob 23 and the proximal portion 26*a* of the outer member 24*a* is coupled to the first knob 22 via a movable member 27. The movable member 27 includes a distal portion 27*a*, a proximal portion 27*b*, and a cannulation 27*c*. The proximal portion 27*b* includes threads 27*b*' on its outer surface 27*b*". The movable member 27 is located in a driver cavity 21*a* of the handle 21. The driver cavity 21*a* includes a distal portion 21*a*' and a proximal portion 21*a*". The proximal portion 21*a*" includes threads 21*b* that engage the threads 27*b*' on the proximal portion outer surface 27*b*". Due to the threaded engagement of the movable member 27 with the proximal portion 21*a*" of the driver cavity 21*a*, rotation of the first knob 22 causes the outer member 24*a* to move axially along the length of the shaft 24. Rotation of the first knob 22 is discontinued when an end 27*a*' of the distal portion 27*a* of the moveable member 27 engages an end 21*c* of the distal portion 21*a*' of the driver cavity 21*a*, thereby preventing over-insertion of the anchor body 13 into the bone. A proximal portion 25*a* of the driver 25 includes threads 25*a*' that engage threads 29 on an inner surface 24*b*' of the inner member 24*b*. Threaded engagement of the driver 25 and inner member 24*b* allow for axial movement of the driver 25 along the shaft 24 via rotation of the second knob 23. Rotation of the second knob 23 is discontinued when a depth stop 25*b* engages an end 24*b*" of the inner member 24*b*, thereby preventing over-insertion of the plug 12 into the tip 11.

Figure 5:
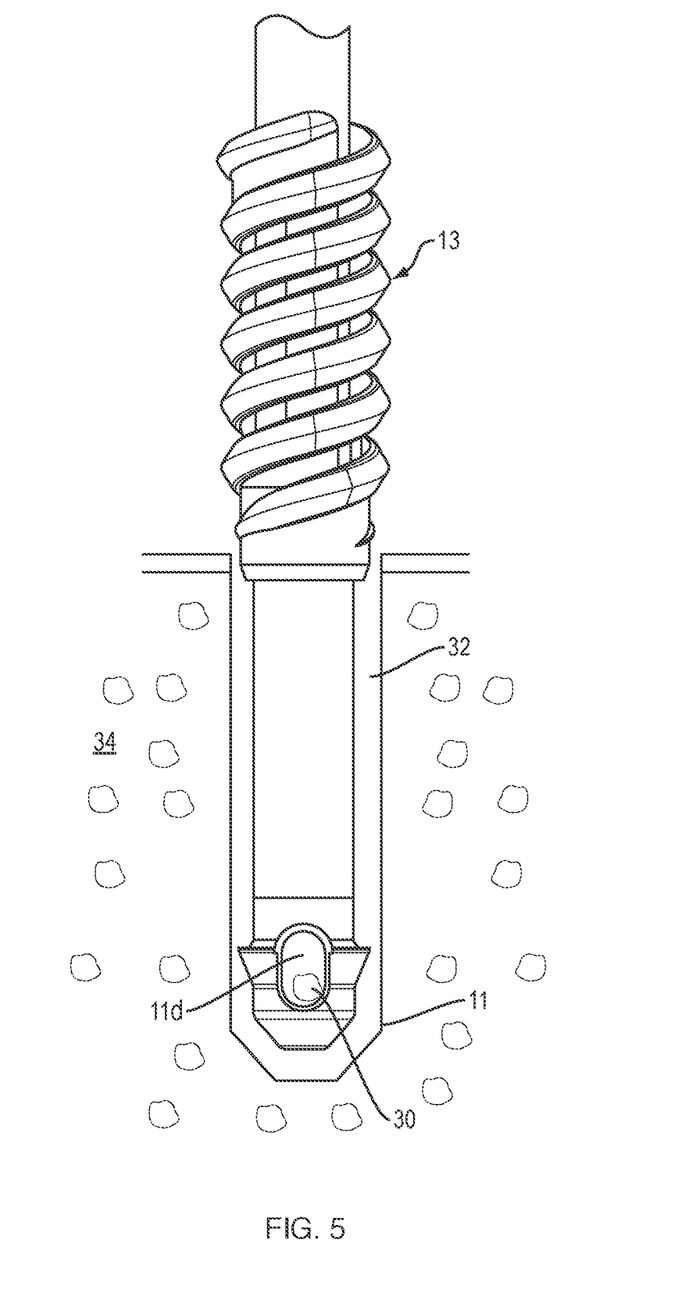
FIGS. 5 and 6 are side views of the anchor assembly of the present disclosure after the anchor assembly is placed within bone.
Figure 6:
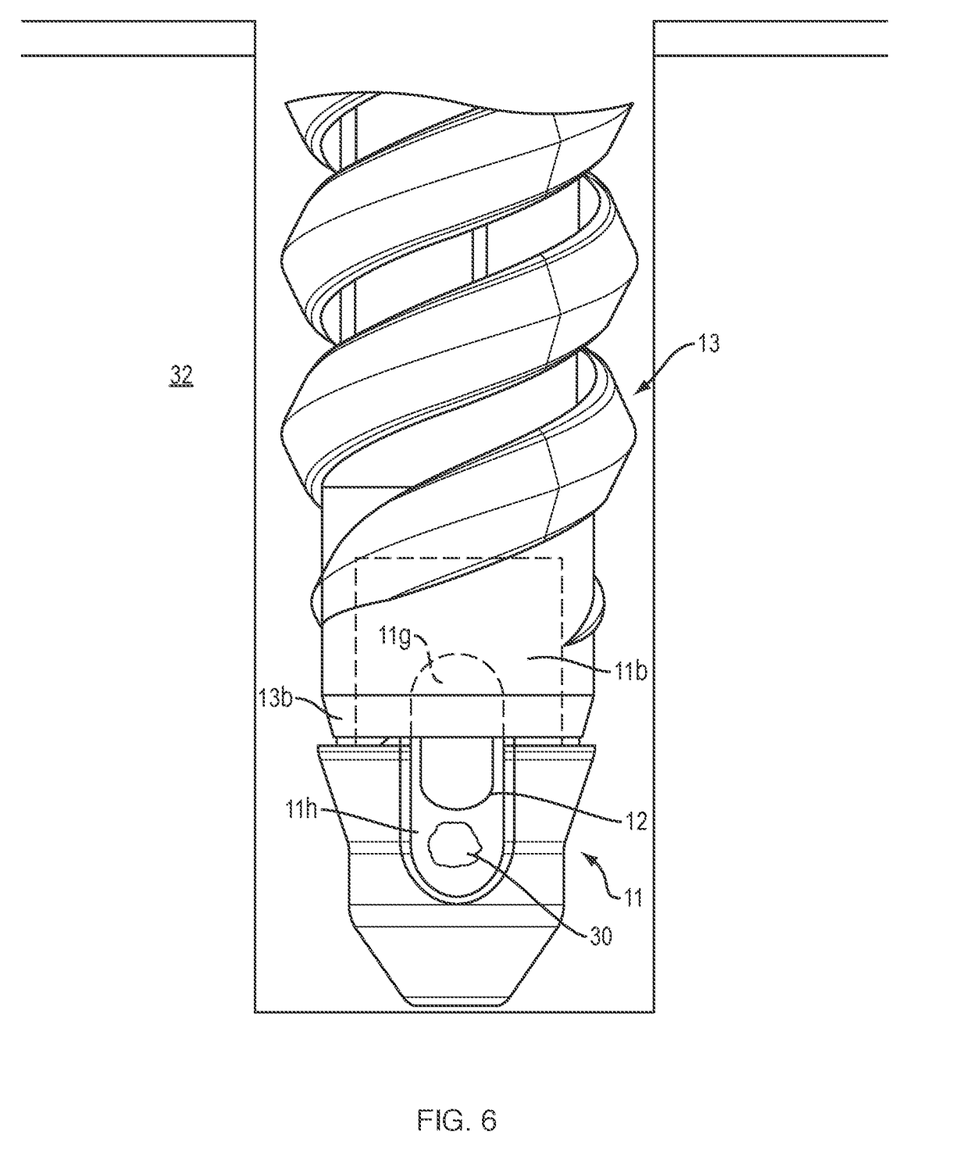

Turning now to FIG. 5, during tissue repair, suture 30 may be initially attached to a soft tissue (not shown). A bone hole 32 is then created in bone 34. Ends of the suture 30 are placed through the through hole 11*d* of the tip 11. The tip 11 is placed within the bone hole 32 via axial advancement (such as malleting) of the delivery device 20. As shown in FIG. 6, the second knob 23 of the delivery device 20 is rotated to move the plug 12 axially to engage and fixate the suture 30 to the tip 11. The first knob 22 of the delivery device 20 is then rotated to move the anchor body 13 axially and place the distal end 13*b* of the anchor body 13 over the proximal portion 11*b* of the tip 11 to further lock the suture 30 between the anchor body 13 and the bone hole 32. Thus, the distal portion 13*b* of the anchor body 13 causes the first region 11*g* of the through hole 11*d* to be occluded and the suture 30 to be further locked within the second region 11*h* of the through hole 11*d*. In examples, the suture 30 may be tensioned prior to advancing the plug 12 to engage the suture 30.

Figure 7A:
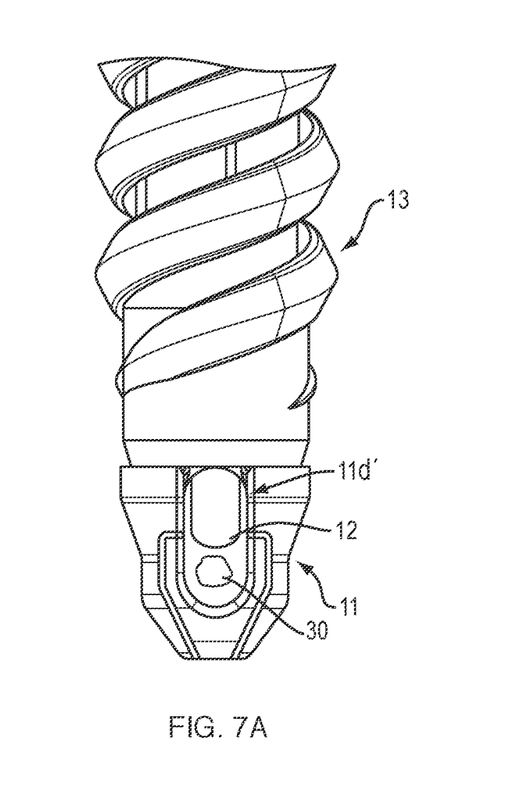
FIGS. 7A and 7B are comparison views between an anchor assembly without an occluded eyelet (FIG. 7A) and the anchor assembly of the present disclosure.
Figure 7B:
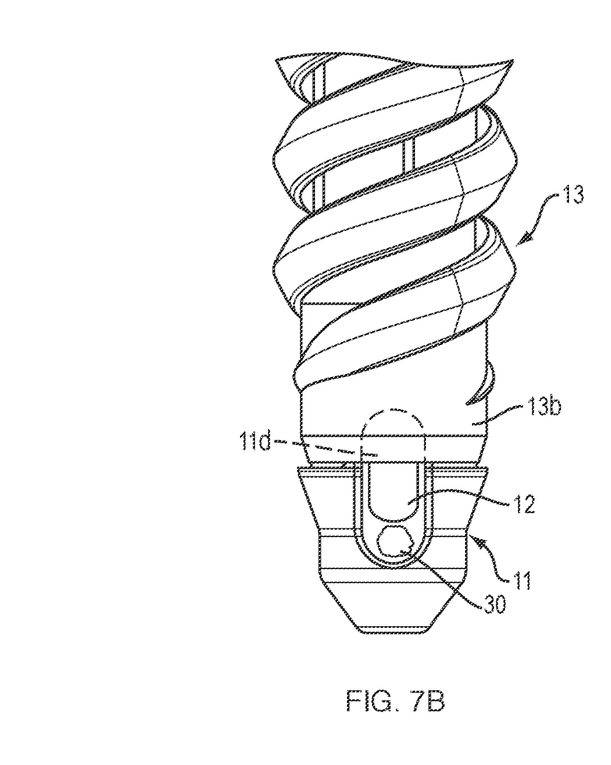

FIGS. 7A and 7B show examples of a through hole 11*d* which is not occluded (FIG. 7A), compared with the occluded through hole 11*d* of this disclosure. Having an occluded through hole 11*d* allows for a larger through hole 11*d* to be defined through the tip 11 which is advantageous for passing a greater amount of suture 30 through the through hole 11*d*. Furthermore, a shorter length of the tip 11 is required in the anchor assembly 10 of this disclosure, which reduces the overall total length of the anchor assembly 10. This in turn beneficially allows for a shallower hole preparation.

The components of the anchor assembly 10 may be made from a polymer material and via an injection molding process. However, other materials and processes may be used. The handle 21 and knobs 22, 23 of the delivery device 20 may be manufactured from a polymer material and via an injection molding process. The handle 21 and knobs 22, 23 may be coupled via an interference fit. However, other materials, processes of making, and methods of coupling may be used. The components of the shaft 24 may be made from a metal material via an extrusion or drawings process. The components of the shaft 24 may be coupled to the handle 21 and the knobs 22, 23 via a threaded fit or an interference fit. However, other materials, processes of making, and methods of coupling may be used.

While the disclosure has been particularly shown and described with references to preferred examples thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

What is claimed is:

1. An anchor assembly comprising:
   a tip comprising:
      a distal portion and a proximal portion;
      a cavity defined within the tip, a wall of the cavity having threads, and an opening of the cavity located in the proximal portion of the tip; and
      a through hole extending through the tip having a first region defined in the distal portion of the tip and a second region defined in the proximal portion of the tip;
   a plug comprising outer threads, the plug disposed within the cavity of the tip such that the threads of a distal region of the plug are engaged with the threads of the cavity and a proximal region of the plug extends from the opening of the cavity; and
   an anchor body disposed about the proximal portion of the tip and enclosing the proximal region of the plug;
   wherein the second region of the through hole is covered by the anchor body and the first region of the through hole is not covered by the anchor body.

2. The anchor assembly of claim 1, wherein the through hole extends through the tip transverse to a longitudinal axis of the cavity.

3. The anchor assembly of claim 1, wherein the plug includes a cannulation.

4. The anchor assembly of claim 1, wherein the anchor body includes a threaded proximal outer portion and a non-threaded distal outer portion.

5. The anchor assembly of claim 4, wherein the non-threaded distal outer portion of the anchor body is coupled to the proximal portion of the tip.

6. The anchor assembly of claim 1, wherein the tip includes a protrusion disposed about an annular surface between the distal portion and a proximal portion of the tip.

7. The anchor assembly of claim 6, wherein an outer diameter of the protrusion is selected to be larger than an outer diameter of the non-threaded distal outer portion of the anchor body.

8. The anchor assembly of claim 1, wherein the through hole is in communication with the cavity defined within the tip.

9. The anchor assembly of claim 1, wherein a distal end of the plug is unthreaded.

10. The anchor assembly of claim 1, further comprising an anchor delivery device comprising:
    a handle having a proximal end and a distal end;
    a first knob coupled to the distal end of the handle;

a second knob coupled to the proximal end of the handle; and a shaft coupled to the handle, the shaft including an outer member, an inner member disposed within the outer member, and a driver disposed within the inner member;

wherein a proximal portion of the driver is coupled to the first knob and a proximal portion of the outer member is coupled to the second knob; and wherein the anchor body is coupled to a distal portion the outer member, the tip is coupled to a distal portion of the inner member, and the plug is coupled to a distal end of the driver.

* * * * *